US00PP29057P2

(12) United States Plant Patent
Arts

(10) Patent No.: US PP29,057 P2
(45) Date of Patent: Mar. 6, 2018

(54) ***HYDRANGEA* PLANT NAMED 'HBA 214903'**

(50) Latin Name: *Hydrangea macrophylla*
Varietal Denomination: HBA 214903

(71) Applicant: Niels Arts, Aalsmeer (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 0 days.

(21) Appl. No.: 15/530,214

(22) Filed: Dec. 12, 2016

(51) Int. Cl.
*A01H 5/02* (2006.01)

(52) U.S. Cl.
USPC ..... Plt./250

(58) Field of Classification Search
USPC ..... Plt./250
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Hydrangea* plant named 'HBA 214903', characterized by its upright plant habit; vigorous growth habit; rapid growth rate; freely branching habit; strong and sturdy stems; freely and uniformly flowering habit; does not require a cold temperature treatment for flower initiation and development; mophead-type inflorescences with numerous pink-colored sterile flowers; and good postproduction longevity.

2 Drawing Sheets

Botanical designation: *Hydrangea macrophylla.*
Cultivar denomination: 'HBA 214903'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HBA 214903'.

The new *Hydrangea* plant is a product of a planned breeding program conducted by the Inventor in De Kwakel, The Netherlands. The objective of the breeding program was to create new freely-branching *Hydrangea* plants with strong sturdy stems, large inflorescences, attractive flower color and good postproduction longevity.

The new *Hydrangea* plant originated from a cross-pollination made by the Inventor in April, 2008 in De Kwakel, The Netherlands, of a proprietary selection of *Hydrangea macrophylla* identified as code number 617, not patented, as the female, or seed, parent with a proprietary selection of *Hydrangea macrophylla* identified as code number 03-0134-055, not patented, as the male, or pollen, parent. The new *Hydrangea* plant was discovered and selected by the Inventor as a single flowering plant from within the progeny of the stated cross-pollination in a controlled greenhouse environment in De Kwakel, The Netherlands in March, 2010.

Asexual reproduction of the new *Hydrangea* plant by vegetative cuttings in a controlled environment in De Kwakel, The Netherlands since June, 2010 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HBA 214903'. These characteristics in combination distinguish 'HBA 214903' as a new and distinct *Hydrangea* plant:

1. Upright plant habit; vigorous growth habit.
2. Rapid growth rate; freely branching habit.
3. Strong and sturdy stems.
4. Freely and uniformly flowering habit; does not require a cold temperature treatment for flower initiation and development.
5. Mophead-type inflorescences with numerous pink-colored sterile flowers.
6. Good postproduction longevity.

Plants of the new *Hydrangea* can be compared to plants of the female parent selection. Plants of the new *Hydrangea* differ primarily from plants of the female parent selection in sterile flower sepal color as plants of the new *Hydrangea* have darker pink-colored sterile flower sepals than plants of the female parent selection.

Plants of the new *Hydrangea* can be compared to plants of the male parent selection. Plants of the new *Hydrangea* differ primarily from plants of the male parent selection in growth habit as plants of the new *Hydrangea* are more vigorous than plants of the male parent selection.

Plants of the new *Hydrangea* can be compared to plants of the *Hydrangea hybrida* 'Agrihydravijf', disclosed in U.S. Plant Pat. No. 19,731. In side-by-side comparisons conducted in De Kwakel, The Netherlands, plants of the new *Hydrangea* differ from plants of 'Agrihydravijf' in the following characteristics:

1. Plants of the new *Hydrangea* are faster-growing than plants of 'Agrihydravijf'.
2. Plants of the new *Hydrangea* have broader leaves than plants of 'Agrihydravijf'.

3. Plants of the new *Hydrangea* do not require a cold treatment for flower initiation and development whereas plants of 'Agrihydravijf' require a cold treatment for flower initiation and development.
4. Plants of the new *Hydrangea* have more sterile flowers per inflorescence than plants of 'Agrihydravijf'.
5. Sepal margins of sterile flowers of plants of the new *Hydrangea* are entire whereas sepal margins of sterile flowers of 'Agrihydravijf' are serrate to crenate.
6. Plants of the new *Hydrangea* have darker pink-colored sterile flower sepals than plants of 'Agrihydravijf'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'HBA 214903'.

The photograph on the second sheet is a close-up view of a typical inflorescence of 'HBA 214903'.

DETAILED BOTANICAL DESCRIPTION

Plants used in the aforementioned photographs and in the following description were grown during the spring in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were five months old when the photographs and description were taken. In the following description, color references are made to The Royal Horticultural Society Colour Chart, 1995 Edition, except where general terms of ordinary dictionary significance are used.

Botanical description: *Hydrangea macrophylla* 'HBA 214903'.

Parentage:

*Female, or seed, parent*.—Proprietary selection of *Hydrangea macrophylla* identified as code number 617, not patented.

*Male, or pollen, parent*.—Proprietary selection of *Hydrangea macrophylla* identified as code number 03-0134-055, not patented.

Propagation:

*Type cutting*.—By vegetative cuttings.

*Time to initiate roots, summer*.—About two weeks at temperatures about 23° C.

*Time to initiate roots, winter*.—About 18 days at temperatures about 18° C.

*Time to produce a rooted young plant, summer*.—About four weeks at temperatures about 23° C.

*Time to produce a rooted young plant, winter*.—About five weeks at temperatures about 18° C.

*Root description*.—Thick; typically whitish brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright plant habit; strong and sturdy stems; rapid growth rate and vigorous growth habit.

*Plant height*.—About 25 cm to 30 cm.

*Plant diameter or area of spread*.—About 25 cm.

Lateral branch description:

*Branching habit*.—Freely branching habit; when pinched, about six to eight lateral branches develop per plant.

*Length*.—About 16 cm to 18 cm.

*Diameter*.—About 4 mm to 5 mm.

*Internode length*.—About 3 cm.

*Texture*.—Smooth, glabrous; fully developed, woody.

*Aspect*.—Upright to about 20° from vertical.

*Strength*.—Strong, sturdy.

*Color*.—Close to 144C, becoming closer to 144A with development; at internodes, close to 187B; lenticels, close to 187B; when woody, close to 177C.

Leaf description:

*Arrangement*.—Opposite, simple.

*Length*.—About 11 cm.

*Width*.—About 8 cm to 10 cm.

*Shape*.—Ovate.

*Apex*.—Acute.

*Base*.—Obtuse.

*Margin*.—Dentate to serrate.

*Texture, upper surface*.—Smooth to rugose, glabrous.

*Texture, lower surface*.—Rugose, glabrous.

*Venation pattern*.—Pinnate.

*Color*.—Developing and fully developed leaves, upper surface: Close to 147B; venation, close to 145B. Developing and fully developed leaves, lower surface: Close to 137D; venation, close to 145D.

*Petioles*.—Length: About 1.5 cm to 2 cm. Diameter: About 3 mm. Texture, upper and lower surfaces: Smooth, glabrous. Color, upper and lower surfaces: Close to 145B.

Flower description:

*Flower type and habit*.—Showy sterile flowers and small, inconspicuous star-shaped fertile flowers arranged on mophead-type terminal panicles; panicles globular and slightly flattened in shape; flowers face upright to outwardly.

*Fragrance*.—None detected.

*Natural flowering season*.—Plants begin flowering about 16 weeks after planting; short production time as a cooling treatment is not required for flower development; continuous flowering from spring to autumn in Northern Europe.

*Flower longevity*.—Sterile flowers last about four months on the plant, sterile flowers persistent; fertile flowers last about one month on the plant, fertile flowers not persistent.

*Quantity of flowers*.—Freely flowering habit; about 70 to 80 sterile flowers per panicle and about 40 to 50 fertile flowers per panicle.

*Panicle height*.—About 6 cm.

*Panicle diameter*.—About 12 cm to 15 cm.

*Sterile flower buds*.—Length: About 3 mm. Diameter: About 3 mm. Shape: Spherical. Color: Close to 155A.

*Fertile flower buds*.—Length: About 3 mm. Diameter: About 3 mm. Shape: Spherical. Color: Close to 62D.

*Sterile flower diameter*.—About 3.5 cm to 4 cm.

*Sterile flower depth* (*height*).—About 1 cm.

*Fertile flower diameter*.—About 6 mm.

*Fertile flower depth* (*height*).—About 6 mm.

*Petals, fertile flowers only, sterile flowers without petals*.—Quantity and arrangement: Five in a single whorl. Length: About 2.5 mm. Width: About 2 mm. Shape: Ovate. Apex: Acute. Base: Cuneate. Margin: Entire. Texture, upper and lower surfaces: Smooth, glabrous. Color: When opening, upper and lower surfaces: Close to 145D. Fully opened, upper and lower surfaces: Close to 62C; color does not change with development.

*Sepals, sterile flowers*.—Quantity and arrangement: Four in a single whorl. Length: About 2 cm. Width: About 2 cm to 2.5 cm. Shape: Deltoid. Apex: Obtuse. Base: Cuneate. Margin: Entire. Texture, upper and lower surfaces: Smooth, glabrous. Color: When opening, upper surface: Close to 144C. When opening, lower surface: Close to 145C. Fully opened, upper and lower surfaces: Close to 69C; towards the base, close to 155B; color becoming closer to 69C with development.

*Sepals, fertile flowers*.—Quantity and arrangement: Five in a single whorl. Length: About 1.5 mm. Width: About 1.5 mm. Shape: Ovate. Apex: Acute. Base: Obtuse. Margin: Entire. Texture, upper and lower surfaces: Smooth, glabrous. Color: When opening, upper and lower surfaces: Close to 145B. Fully opened, upper and lower surfaces: Close to 145B; color does not change with development.

*Pedicels, sterile flowers*.—Length: About 1.5 cm. Diameter: About 2 mm. Strength: Strong. Aspect: About 45° from vertical. Texture: Smooth, glabrous. Color: Close to between 157D and 69C.

*Pedicels, fertile flowers*.—Length: About 5 mm. Diameter: About 1 mm. Strength: Strong. Aspect: Mostly upright. Texture: Smooth, glabrous. Color: Close to 69C.

*Reproductive organs, fertile flowers only; sterile flowers without reproductive organs*.—Stamens: Quantity per flower: Eight. Filament length: About 1 mm. Filament color: Close to 155D. Anther shape: Conical. Anther length: About 1 mm. Anther color: Close to 63C. Pollen amount: Abundant. Pollen color: Close to 1.55D. Pistils: Pistil quantity per flower: Three. Pistil length: About 3 mm. Stigma shape: Oval. Stigma color: Close to 69B. Style length: About 1 mm. Style color: Close to 69B. Ovary color: Close to 69C.

*Seeds*.—Quantity per flower: About 20 to 30. Length: About 0.5 mm. Diameter: About 0.1 mm. Color: Close to 200C.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 3° C. to about 38° C.

It is claimed:

1. A new and distinct *Hydrangea* plant named 'HBA 214903' as illustrated and described.

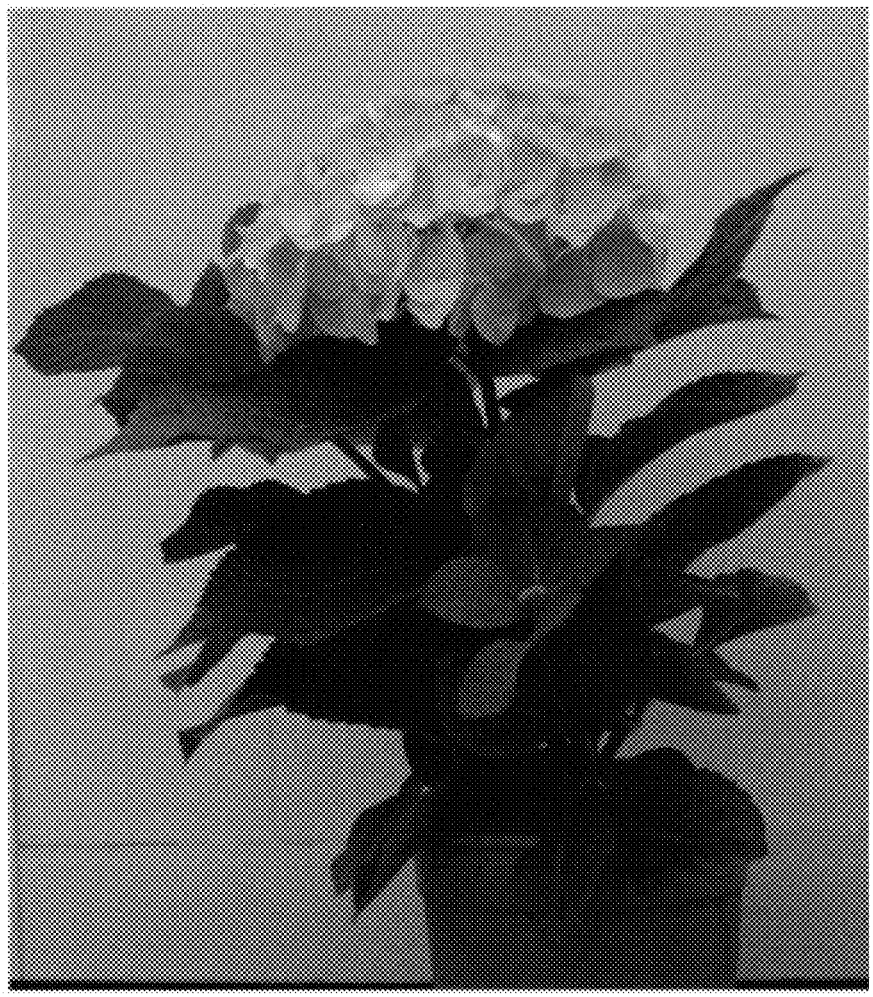

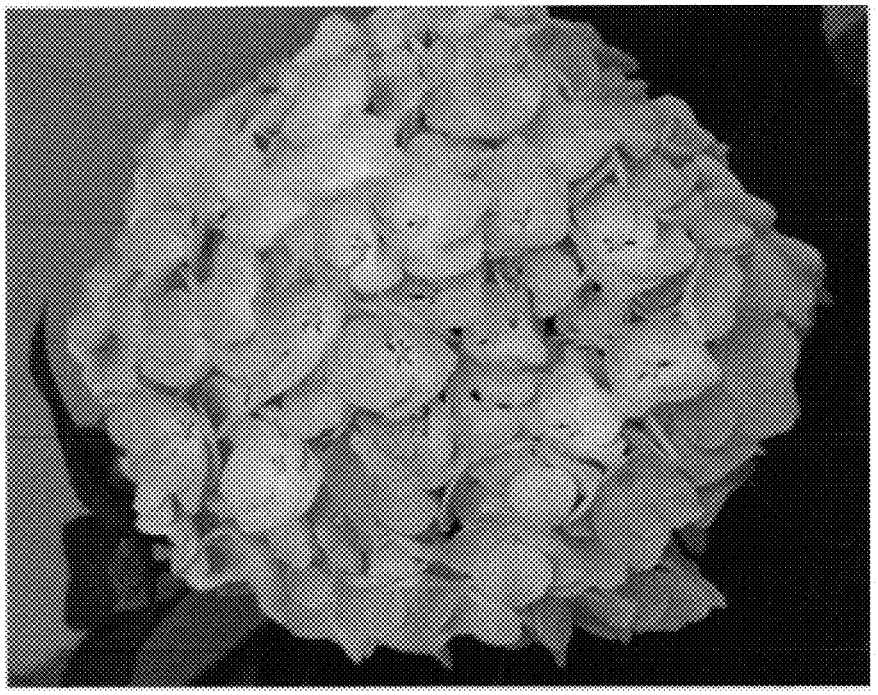

* * * * *